US012011519B2

United States Patent
Sward et al.

(10) Patent No.: US 12,011,519 B2
(45) Date of Patent: *Jun. 18, 2024

(54) AIR SCENTING APPLIANCE FOR A VEHICLE

(71) Applicant: Prolitec Inc., Seattle, WA (US)

(72) Inventors: Nathan Sward, Wauwatosa, WI (US);
Matthew Ansley, Muskego, WI (US);
Richard Weening, Seattle, WA (US);
Juan Moncada, Seattle, WA (US)

(73) Assignee: Prolitec Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/128,091

(22) Filed: Mar. 29, 2023

(65) Prior Publication Data

US 2023/0277715 A1 Sep. 7, 2023

Related U.S. Application Data

(63) Continuation of application No. 17/714,927, filed on Apr. 6, 2022, now Pat. No. 11,660,366.

(Continued)

(51) Int. Cl.
*A61L 9/00* (2006.01)
*A61L 9/14* (2006.01)
(Continued)

(52) U.S. Cl.
CPC .............. *A61L 9/14* (2013.01); *B60H 3/0007* (2013.01); *A61L 2209/11* (2013.01)

(58) Field of Classification Search
CPC ...... A61L 9/14; A61L 2/10; A61L 9/12; B01F 3/04049; B65D 83/60
(Continued)

(56) References Cited

U.S. PATENT DOCUMENTS 7,712,683 B2 5/2010 Robert et al.
7,930,068 B2 4/2011 Robert et al.
(Continued)

FOREIGN PATENT DOCUMENTS

CN 206959190 U 2/2018
CN 112023105 A 12/2020
(Continued)

OTHER PUBLICATIONS

Invitation to Pay Additional Fees, mailed Jul. 22, 2022, for International Application No. 1 PCT/US2022/024115, 42 pages.
(Continued)

*Primary Examiner* — Monzer R Chorbaji
(74) *Attorney, Agent, or Firm* — Seed IP Law Group LLP

(57) ABSTRACT

An air scenting system for a vehicle is provided which includes an appliance and a replaceable cartridge installable therein. The replaceable cartridge contains a liquid compound to be aerosolized and has a cartridge outlet through which the aerosolized compound is discharged during operation. A pump is provided to supply air to the replaceable cartridge to generate the aerosolized compound from the liquid compound contained in the replaceable cartridge, and a controller is provided for controlling the pump to supply the air to the replaceable cartridge to generate and discharge the aerosolized compound from the appliance. The appliance is particularly adapted for dispensing scent into the interior space of a vehicle, and includes a form factor particularly well suited for positioning the appliance in a cup holder. Additionally, the appliance is designed for use in vehicles when a driver is present and readily adjustable by the driver to provide a uniform scent experience.

19 Claims, 5 Drawing Sheets

Related U.S. Application Data

(60) Provisional application No. 63/173,475, filed on Apr. 11, 2021.

(51) Int. Cl.
  *B01D 47/02* (2006.01)
  *B60H 3/00* (2006.01)
  *F02M 45/10* (2006.01)

(58) Field of Classification Search
  USPC ............... 422/305–306; 261/76; 239/1, 93
  See application file for complete search history.

(56) References Cited

U.S. PATENT DOCUMENTS

| | | | |
|---|---|---|---|
| 8,855,827 | B2 | 10/2014 | Weening et al. |
| 9,162,004 | B1 | 10/2015 | Ansley et al. |
| 9,248,461 | B2 | 2/2016 | Ansley et al. |
| 9,745,976 | B2 | 8/2017 | Ansley et al. |
| 9,797,396 | B2 | 10/2017 | Ansley et al. |
| 10,010,640 | B1 | 7/2018 | Li |
| 10,086,340 | B2 | 10/2018 | Ansley et al. |
| 10,294,935 | B2 | 5/2019 | Ansley et al. |
| 10,512,706 | B2 | 12/2019 | Avidor |
| 10,690,104 | B1 | 6/2020 | Awadi et al. |
| 10,869,944 | B2 | 12/2020 | Avidor |
| 11,052,356 | B2 | 7/2021 | Ansley et al. |
| 11,083,813 | B2 | 8/2021 | Avidor |
| D948,020 | S | 4/2022 | Bibi et al. |
| 2008/0006651 | A1 | 1/2008 | Arakawa et al. |
| 2010/0266266 | A1 | 10/2010 | Garcia Fabrega et al. |
| 2017/0360979 | A1 | 12/2017 | Avidor |
| 2017/0360981 | A1 | 12/2017 | Avidor |
| 2018/0028985 | A1* | 2/2018 | Ansley ............... A61L 9/14 |
| 2020/0171193 | A1 | 6/2020 | Avidor |
| 2020/0171195 | A1 | 6/2020 | Sevy |
| 2021/0000307 | A1 | 1/2021 | Venturino |

FOREIGN PATENT DOCUMENTS

| | | |
|---|---|---|
| CN | 112092583 A | 12/2020 |
| CN | 212649821 U | 3/2021 |
| JP | 2007022487 A | 2/2007 |
| JP | 2013203354 A | 10/2013 |
| WO | WO 2017073134 A1 | 5/2017 |
| WO | WO 2018022660 A2 | 2/2018 |
| WO | WO 2022109159 A1 | 5/2022 |

OTHER PUBLICATIONS

International Search Report and Written Opinion, mailed Dec. 2, 2022, for International Application No. PCT/US2022/024115, 152 pages.

\* cited by examiner

AIR SCENTING APPLIANCE FOR A VEHICLE

CROSS-REFERENCE TO RELATED APPLICATIONS

This application is a continuation of U.S. patent application Ser. No. 17/714,927, filed Apr. 6, 2022, which claims the benefit of U.S. Provisional Patent Application No. 63/173,475, filed Apr. 11, 2021, the entire disclosure of which is herein incorporated by reference for all purposes.

BACKGROUND

Technical Field

The present disclosure relates generally to air scenting appliances and, more specifically, to air scenting appliances for vehicles that include a replaceable scent cartridge containing a liquid scent compound to be diffused or aerosolized and released into the vehicle. The air scenting appliances are particularly well suited to be positioned within a cup holder of a vehicle and operated within the confines of an interior of the vehicle. The air scenting appliances are specifically designed for use in vehicles when a driver is present and readily adjustable by the driver to provide a uniform scent experience.

Description of the Related Art

Air scenting appliances in the past have had the ability to dispense scent compounds or other compounds throughout the atmosphere of desired spaces but can suffer from various drawbacks or deficiencies. For example, some air scenting appliances and replaceable cartridges thereof may be overly complex, costly and/or suffer from other deficiencies or drawbacks, such as, for example, discharging diffused or aerosolized matter with less than ideal characteristics, or the cartridges being susceptible to leakage, tampering, fouling and/or contamination. In addition, many known air scenting appliances are not particularly well suited to be used within confined spaces such as the interior of a vehicle or where there are frequently changing airflow conditions therein. Moreover, many known air scenting appliances are not particularly well suited to enable operation and adjustment thereof by a driver operating a motor vehicle in a safe and efficient manner.

BRIEF SUMMARY

The air scenting appliances for vehicles and replaceable cartridges and other components thereof and related methods shown and described herein provide form factors that are robust, efficient, and particularly effective at treating confined spaces of a vehicle with a diffused or aerosolized compound from a liquid source, and include air scenting appliances that are specifically configured to be positioned within a cup holder of a vehicle. Moreover, the air scenting appliances for vehicles are particularly well suited for safe and effective operation by a driver while driving and are readily controllable to adjust output to account for changing airflow conditions that are present within the vehicle as well as occupant preferences.

DETAILED DESCRIPTION

In the following description, certain specific details are set forth in order to provide a thorough understanding of various disclosed embodiments. However, one skilled in the relevant art will recognize that embodiments may be practiced without one or more of these specific details. In other instances, well-known devices, structures and techniques associated with air scenting appliances (also referred to as liquid scent diffusion devices), components thereof and related methods of diffusing or aerosolizing a compound from a liquid scent source may not be shown or described in detail to avoid unnecessarily obscuring descriptions of the embodiments. For example, embodiments of the air treatment appliances and replaceable cartridges disclosed herein may include or incorporate aspects or features of known appliances and associated components and control methods thereof. Examples of known air scenting appliances, components and aspects thereof and related methods are shown and described in U.S. Pat. Nos. 7,712,683; 7,930,068; 8,855,827; 9,248,461; 9,162,004; and 10,086,340, all of which are incorporated herein by reference in their entirety.

Unless the context requires otherwise, throughout the specification and claims which follow, the word "comprise" and variations thereof, such as "comprises" and "comprising," are to be construed in an open, inclusive sense, that is, as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

Figure 1:
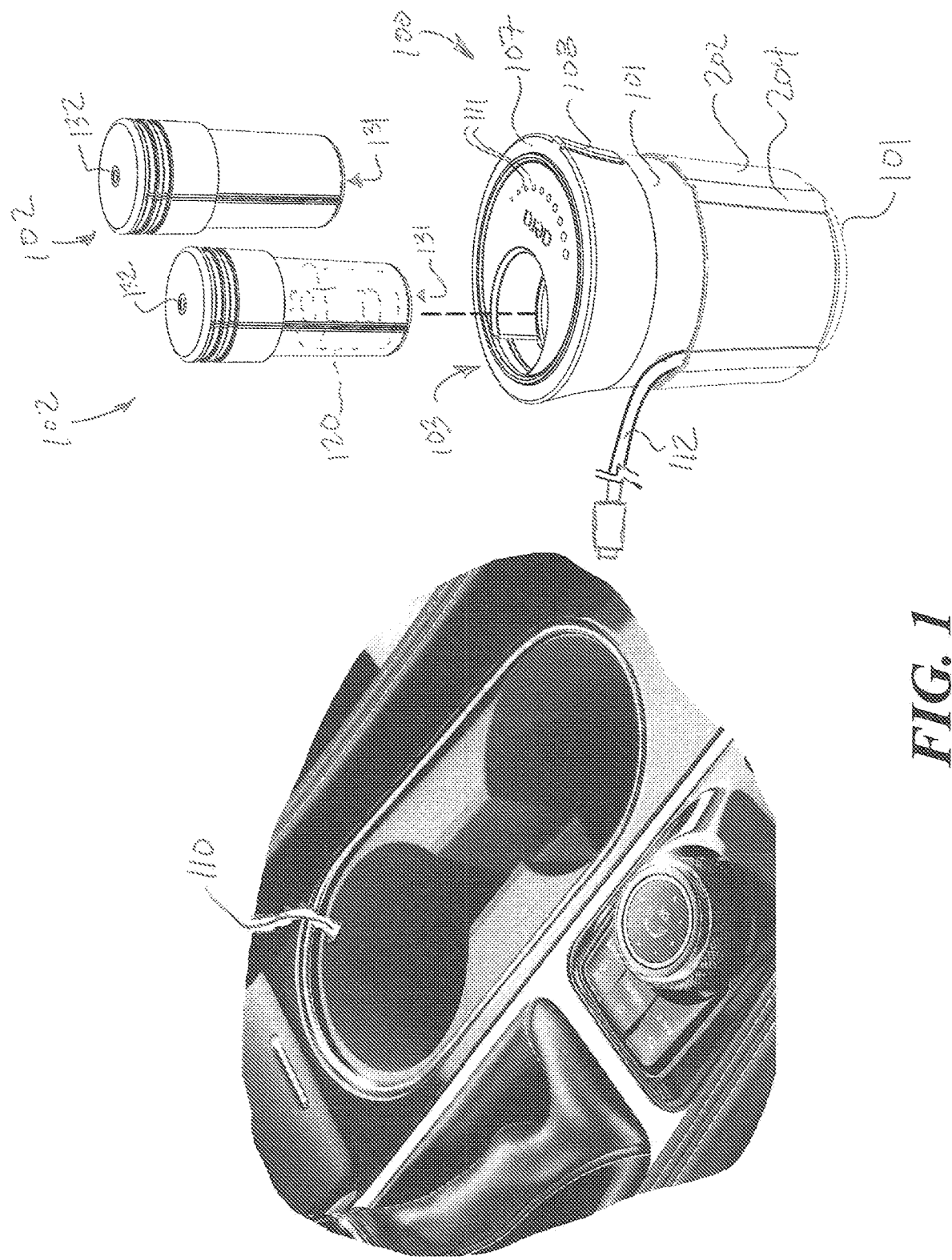
FIG. 1 is an isometric view of an air scenting system, according to one embodiment, including an air scenting appliance for treating an interior of a vehicle with a scent compound diffused or aerosolized from a liquid contained in replaceable cartridges that may be loaded in the appliance.
Figure 3:
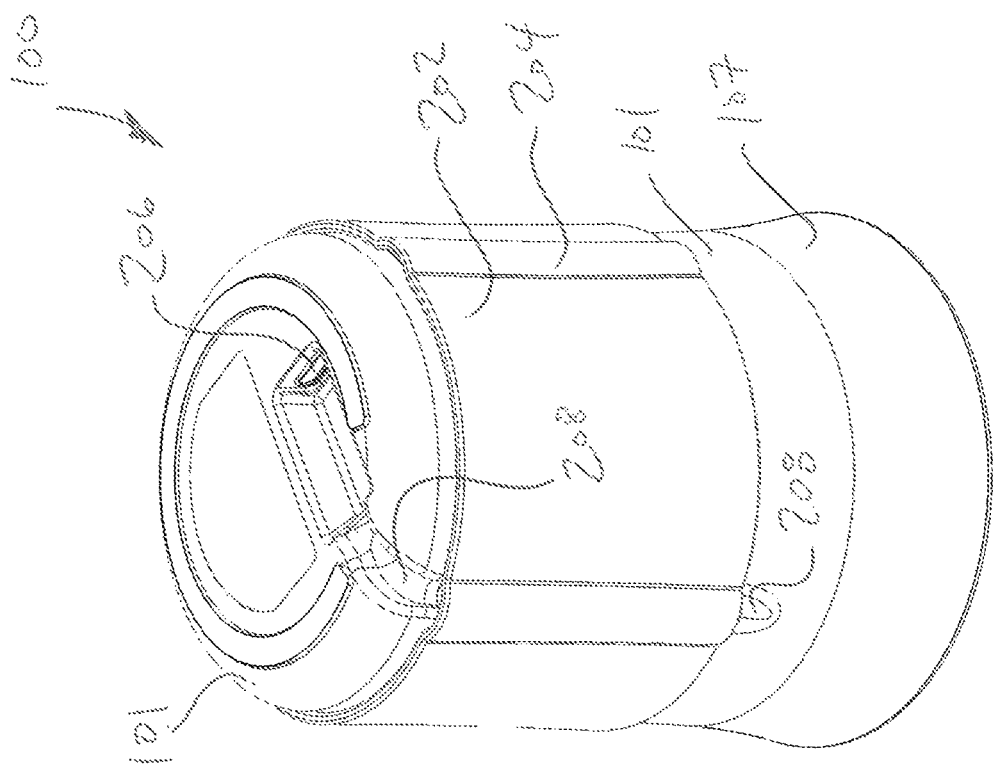
FIG. 3 is a bottom isometric view of the air treatment appliance of FIG. 1.
Figure 2:
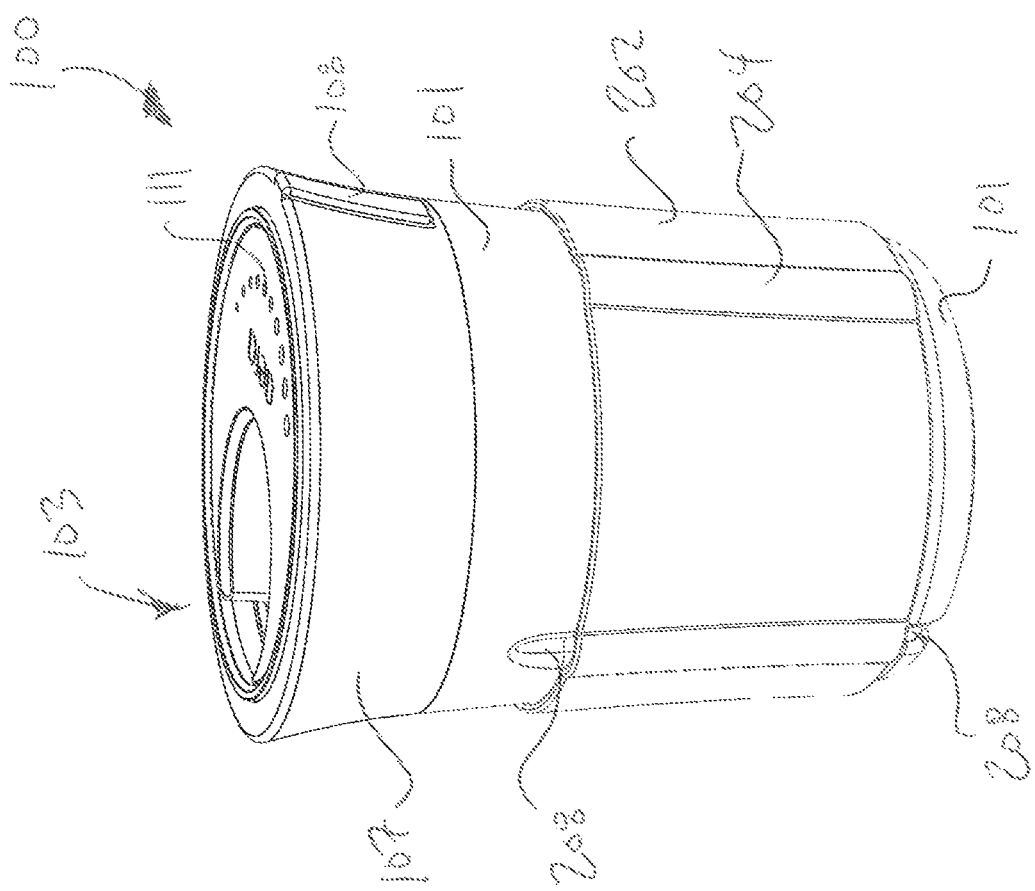
FIG. 2 is a top isometric view of the air treatment appliance of FIG. 1.

With reference to FIG. 1, the present disclosure relates generally to air scenting appliances 100 and more specifically to air scenting appliances 100 operable with replaceable cartridges 102 containing a liquid scent compound 120 to be diffused or aerosolized and released into an interior of a vehicle to be treated, which may also referred to as liquid diffusion devices or apparatuses, and to components thereof and related methods.

As shown in FIG. 1, the air scenting appliances 100 of the present disclosure may be provided in a form factor that is configured for use in the interior space of a vehicle (i.e., a car interior) for treating the interior space with a scent compound or other compound diffused or aerosolized from a liquid source. In particular, the appliances 100 may include a form factor that is configured to be readily inserted in a cup holder 110 within the interior of a vehicle. It is also appreciated, however, that the appliances 100 are portable in nature and may be relocated as desired to treat different spaces.

With continued reference to FIG. 1, each replaceable cartridge 102 includes a cartridge outlet 132 to permit a diffused or aerosolized compound generated from the liquid 120 within the cartridge 102 to be discharged into the environment or space surrounding the appliance 100. More particularly, when loaded, the replaceable cartridge 102 within the appliance 100 is coupled to an outlet of a source of pressurized air (e.g., pump 122 of FIG. 4) to enable pressurized air to be selectively passed through the cartridge 102 as described herein to diffuse or aerosolize the liquid 120 contained therein and to force the aerosolized matter to be discharged through the cartridge outlet 132.

Within the present disclosure, the terms atomize and diffuse may be used in their various forms interchangeably. They are intended to refer to generally the same action, that being the dispersion of liquid into very small particle sizes (preferably but not limited to one micron or less in size) and releasing the particles into the atmosphere of a generally enclosed space. Discharging diffused liquid with particularly small particles helps ensure that the liquid to be dispersed remains airborne long enough to effectively treat the space. The diffused liquid is also referred to herein as aerosolized matter, and may include, for example, a scented compound.

One approach to providing small particle sizes is to incorporate a dispersion or gas-liquid mixing location adjacent an expansion chamber. The mixed gas and liquid combination may contain particles of greater than desirable size. Allowing this mix to remain resident within the expansion chamber prior to release into the treated space will allow larger particles to precipitate out of the mixture. Structures that the gas and liquid mixture impinge upon may also assist in the collection of these larger particles and leave only the desired predominantly smaller sized particles to be released. The expansion chamber may be maintained at a positive pressure with respect to the atmospheric pressure within the space to be treated, so that the gas and liquid mix will be ejected from the appliance 100 into the space. Alternatively, the expansion chamber may generally be maintained at the atmospheric pressure of the space to be treated with the flow of gas (e.g., air) through the chamber providing the impetus for movement of the gas and liquid mix from the cartridge 102 of the appliance 100 into the space to be treated.

Within the context of this disclosure, diffusion or aerosolizing also generally refers to a process or method of dispersing a liquid without destroying the integrity of the liquid compound. While some degree of reactivity between the gas (e.g., air) and the liquid may be desirable, diffusion generally does not change the nature of the liquid, unlike heating or the application of electrical energy into the liquid to diffuse the liquid.

Within the context of this disclosure, the air scenting appliances 100 use an air pump (e.g., pump 122) and a venturi (e.g., venturi device 142) to convert liquid-state fragrance formulations into an adjustable quantity of micro-droplets which transition to vapor immediately (85 to 300 ms) after exiting the appliance 100. This vapor becomes invisible as it blends into the ambient air to create scent effect. The quantity of droplets exiting the appliance 100 determine the strength of the scent as perceived by human occupants. The number of scent molecules vs mols of air is expressed in grams per cubic meter ($g/cu^3$ or PPM parts per million). This is the "concentration" of scent in the air. The more scent molecules in the ambient air the stronger the scent effect.

One challenge addressed by embodiments of the present invention relates to changing airflow conditions within a vehicle that significantly impact the concentration of scent in the air of the vehicle and thus the perceived strength of the scent, a key part of the scent experience. Airflow conditions in a vehicle change frequently with changes in, for example, driving speed, air handler fan speed, ambient temperature and humidity, and proportion of fresh versus recirculated air. Compounding the unavoidable changes in airflow condition is occupant scent perception thresholds. The ability to perceive scents changes, for example, with age and gender. While what is desired by one person can be established and locked in for a single driver, other occupants may require something different ranging from no scent to a strong scent.

Accordingly, it is believed that to be an effective air scenting or freshening device, the driver must be able to adjust the quantity of droplets in the air (i.e., the scent concentration) to ensure a pleasant and uniform experience in varying airflow conditions and varying occupant preferences. Air freshening approaches of the prior art which cannot adjust output will produce widely different experiences and optimizing the scent experience for various occupant preferences is not possible.

Another challenge addressed by embodiments of the present invention relates to operational safety. How does a driver adjust a scenting experience without taking their eyes off the road? According to embodiments of the present invention, the appliance 100 fits snuggly in a cup holder of a vehicle conveniently within arm reach of a driver in a consistent and known position. On the upper end of the appliance 100, there is provided an adjustment device in the form of an annular dial around the circumference of the appliance 100 which can be conveniently turned in increments (e.g., in increments from 0 (no output) to 10 (maximum output)) with the thumb and forefinger of the driver's hand. Advantageously, in a preferred implementation, an audible progressively louder audible indication (e.g., click) confirms each setting step from one step to the next from no output to maximum output. In addition, or in lieu thereof, tactile feedback (e.g., vibrations, detent engagements) may be provided to indicate the intensity setting. This is particularly advantageous in enabling a driver to adjust the scent output of the appliance 100, and hence scent concentration within the vehicle, to adjust for changing air conditions within the vehicle and/or occupant preferences without compromising safe driving habits.

Notably, the air scenting appliances 100, replaceable cartridges 102 and other components and methods described herein may be used to provide or introduce a pleasant or soothing scent into the air space of a vehicle or other generally enclosed space. The particular liquid 120 to be dispensed by the scenting appliance 100 is contained within the replaceable cartridge 102. Although embodiments of the invention are described in the context of discharging scents, the present disclosure is not necessarily limited to a particular type or nature of liquid 120 to be dispersed, but is intended to encompass any desirable airborne liquid treatments that are preferably dispersed within an enclosed space to be effective. The term enclosed space, as used herein, refers to any volume of space within which the atmospheric turnover is sufficiently slow to permit the dispersed liquid to have its desired effect within the space. Some spaces may have one or more openings and still have the desired characteristics to permit treatment with a diffused liquid. Other spaces may be preferably fully enclosed to permit treatment by the selected liquid. In other cases, the liquid used for treatment may preferably be used in a sealed space, for maximum effectiveness or for safety reasons. Within the scope of the present disclosure, it is not intended to limit the nature, size or configuration of the space to be treated except as may be appropriate for the liquid used to treat the space and the nature of treatment desired within the space. That said, embodiments described herein are particularly well suited for treating the interior space of a vehicle, which may be fully enclosed or in some instances have one or more openings such as one or more open windows. In addition, as described earlier, the interior space of the vehicle may particularly prone to changing airflow conditions, and the embodiments disclosed herein may be particularly well suited to enable dynamic adjustment of scent output to provide a more uniform scent experience despite such variable airflow conditions.

Figure 4:
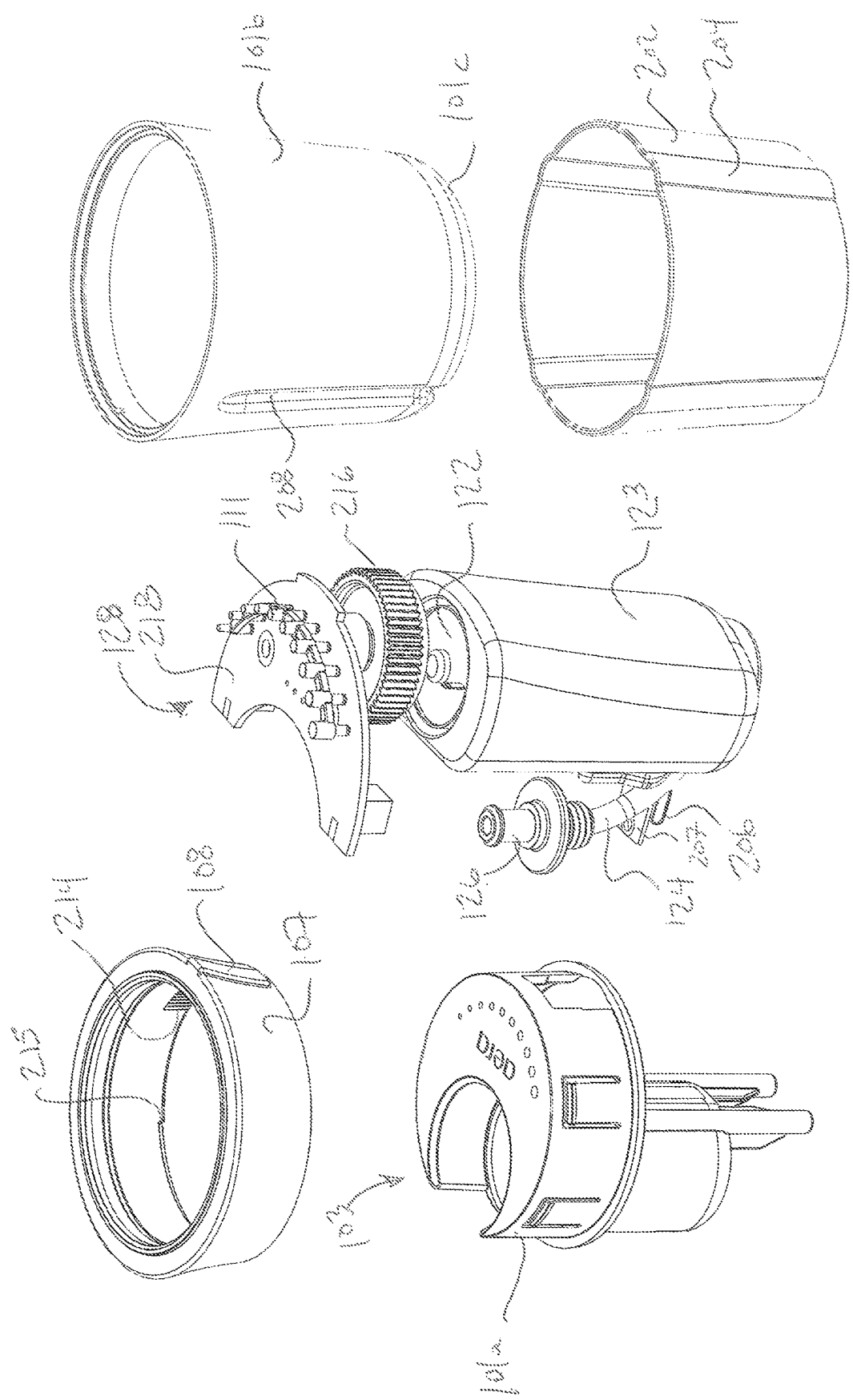
FIG. 4 is an isometric exploded view of the air treatment appliance of FIG. 1.

With reference to FIG. 4, and according to the illustrated embodiment, a control system 128 (inclusive of a printed circuit board, PCB, 218) is provided and is configured to permit adjustment of the timing, flow rate and/or pressure level of the pressurized air generated by a pump assembly 122 that is directed into and passes through an installed cartridge 102 during use. In some instances, the operating pressure may be relatively low, such as, for example, less than about 2 psi gauge pressure or about 1.5 psi gauge pressure. Within the cartridge 102, the pressurized air is directed to atomize the liquid 120 contained therein and to aid in the dispersion of the atomized liquid into the air space to be treated.

In some instances, it may be desirable to have an indirect route from the point of actual atomization of the liquid and a cartridge outlet 132 through which atomized particles exit from the cartridge 102. As will be described in greater detail elsewhere, embodiments of the replaceable cartridges 102 described herein provide an atomization zone where liquid 120 from the cartridge 102 and pressurized air meet and are mixed. In addition, the cartridges 102 may also provide an expansion chamber or chambers within the cartridge 102 where the atomized liquid is retained until a portion of the atomized liquid is allowed to exit the cartridge 102 loaded in the host appliance 100. As described in greater detail elsewhere, the cartridges 102 may combine storage of the liquid 120 to be diffused, an atomization structure to transform the liquid 120 into an airborne concentration, an expansion chamber or chambers, and optionally a tortuous path or passage towards the outlet 132 of the cartridge 102.

With reference to FIGS. 1 through 4, one example embodiment of an air scenting appliance 100 is illustrated and includes an appliance housing 101 configured to receive the cartridges 102 therein. As previously discussed, the appliance 100 is configured to treat a space with a diffused or aerosolized scent compound generated by a flow of air moving through the cartridge 102 which is entrained with liquid particles from liquid 120 contained in the cartridge 102. For this purpose, the appliance 100 may include one or more controls, such as, for example, a rotational dial 107 which may act as a power on/off control for powering up and powering down the appliance 100, as well as an intensity control for adjusting the intensity or quantity of discharged matter into the surrounding environment. In one specific implementation, for example, the rotational dial 107 may be configured to rotate in incremental steps from 0 (no output) to 10 (maximum output). The appliance 100 may further include one or more indicators 111 (e.g., LEDs) for providing operational feedback signals, such as, for example, an intensity level at which the appliance 100 is operating. In addition or in lieu of such indicators 111, the appliance 100 may include one or more features to provide audible feedback (e.g., clicks, beeps, or other sounds) of adjustments in intensity level and/or haptic feedback (e.g., vibrations, detent engagements) of adjustments in intensity level. The magnitude, duration or intensity of the audible and/or haptic feedback may change from one step in intensity level to the next. Intensity may vary in a stepwise or continuous manner and changes in the audible and/or haptic feedback may be correspondingly provided in a stepwise or continuous manner.

The appliance 100 may further include a cable 112 for connecting the appliance 100 to a power supply, such as a power supply of a host vehicle, and/or for coupling the appliance to the electrical system of the vehicle for the transfer of data signals. In other embodiments, the appliance 100 may include an onboard power supply, such as an onboard rechargeable battery or battery pack, to facilitate use of the appliance 100 in a location that may be remote from a power outlet or other external power source.

As shown in FIG. 4, the housing 101 may include a plurality of housing components 101a, 101b, 101c that combine together to form the housing 101. The housing components 101a, 101b, 101c of the illustrated embodiment include, for example, an upper housing component 101a which defines a cartridge receiving cavity 103 for receiving the cartridges 102. The housing components 101a, 101b, 101c of the illustrated embodiment further include a mid-housing component 101b which defines a substantial portion of an external profile of the appliance 100 and which accommodates various functional components of the appliance 100. For example, the mid-housing component 101b surrounds the pump 122, which is configured to supply a flow of air to the cartridge 102 during operation via a gas supply conduit 124 and stem 126 that is provide at the end of the gas supply conduit 124. The stem 126 is supported within the cartridge receiving cavity 103 of the upper housing component 101a and is sized and shaped to be insertably received in a bottom end of a loaded cartridge 102. The housing components 101a, 101b, 101c of the illustrated embodiment further include a lower housing component 101c that provides a stable base for the appliance 100 and supports an electrical port 206 and associated circuit board 207 at a lower end of the appliance 100 for supplying power to the appliance 100 and/or exchanging data signals.

Figure 5:
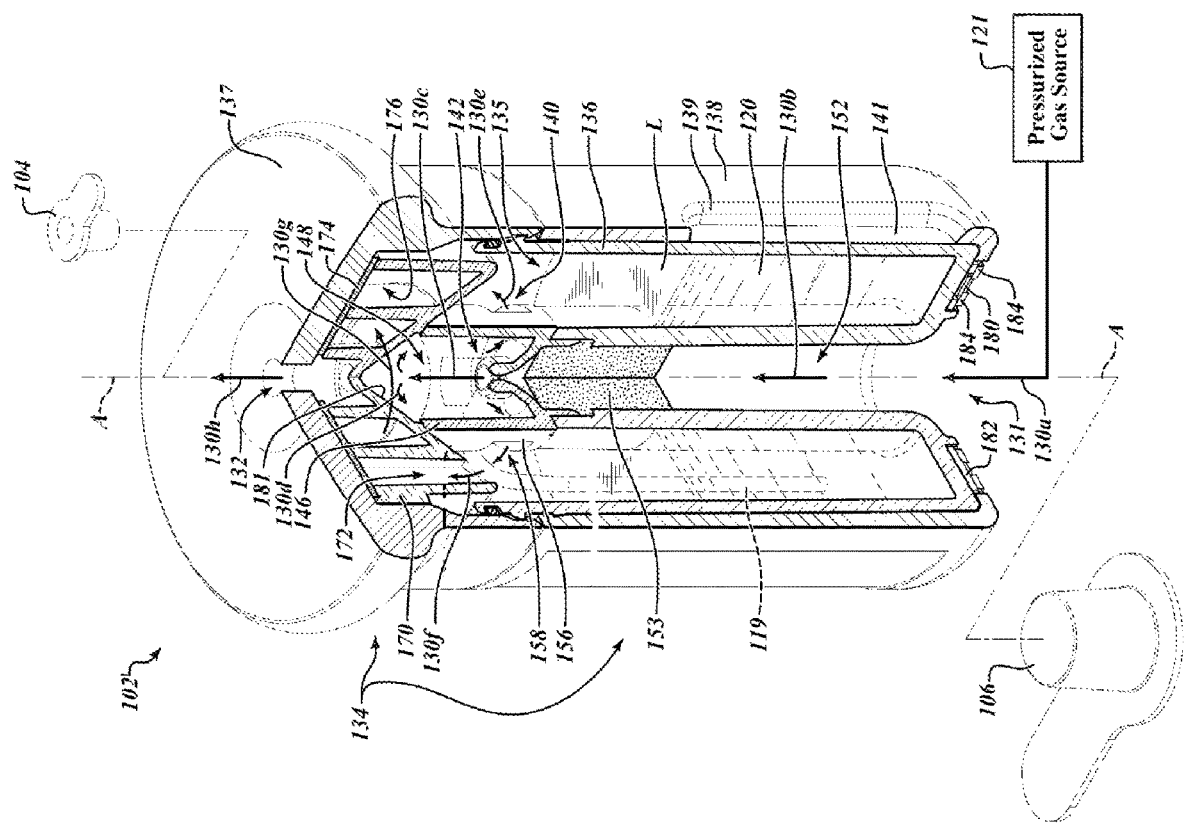
FIG. 5 is an isometric cross-sectional view of an example replaceable cartridge usable with the air treatment appliance of FIG. 1.

FIG. 5 shows further details of a cartridge 102' that is substantially similar to the cartridges 102 illustrated in FIG. 1, and which may be insertably received in the appliance 100 to provide a source of the liquid 120 to be aerosolized. With reference to FIG. 5, the replaceable cartridge 102' may include a cartridge housing 134 comprising a plurality of housing pieces coupled together to define a fluid receptacle having an internal cavity 135, which is partially filled with the liquid 120 to be diffused. For example, in accordance with the example embodiment of the cartridge 102' shown in FIG. 5, the cartridge housing 134 includes an internal housing body 136 defining at least a portion of a receptacle for the liquid 120 to be aerosolized, an upper housing cap 137 including the cartridge outlet 132 through which the aerosolized matter is discharged during use, and an outer casing 138 surrounding at least a lower portion of the internal housing body 136. In some instances, at least some of the housing pieces, for example, the internal housing body 136 and the upper housing cap 137, may be fixedly coupled together to prevent non-destructive disassembly of the cartridge 102', making it effectively tamperproof. This may be desirable to prevent users from refilling and reusing a spent cartridge that may be ineffective or less effective in treating the space due to fouling or build-up of residue within the cartridge 102' from prior use.

As an example, and with reference to FIG. 5, the internal housing body 136 and the upper housing cap 137 may be provided with interlocking structures that snap or otherwise couple together in a manner that prevents non-destructive disassembly of the cartridge housing 134. A seal, such as an o-ring seal or other seal, may be provided between the internal housing body 136 and the upper housing cap 137 near the interlocking structures to provide a liquid tight seal when the cartridge housing 134 is assembled. In this manner, the liquid 120 to be diffused may be prevented from leaking from the cartridge housing 134 at an interface between the internal housing body 136 and the upper housing cap 137. Upon depletion of the liquid 120, the cartridge 102' may be readily removed and replaced with a like cartridge 102' for continued treatment of the environment surrounding the host appliance 100, and the depleted cartridge 102' may be discarded as an intact unit or collected for refurbishment purposes.

With continued reference to FIG. 5, the internal housing body 136 and the outer casing 138 may be provided with interlocking structures that couple together in a manner that prevents disassembly of the outer casing 138 from the internal housing body 136 until a threshold resistive force is overcome, after which the outer casing 138 may be removed from the internal housing body 136. In other instances, the interlocking structures may prevent non-destructive disassembly of the outer casing 138 from the remainder of the cartridge 102' to further assist in making the cartridge 102' tamperproof.

In accordance with the example embodiment of the replaceable cartridge 102' shown in FIG. 5, the internal housing body 136 may be transparent or semi-transparent and the outer casing 138 may be opaque, and the outer casing 138 may be provided with a window 139 through which a level L of the liquid 120 to be aerosolized is viewable through an exposed portion 141 of the transparent or semi-transparent internal housing body 136. Advantageously, the window 139 of the outer casing 138 may have a size and a shape sufficient to observe the liquid level L of the liquid 120 in the internal housing body 136 as the liquid 120 transitions between a full level and an empty level. In this manner, a user can retrieve the cartridge 102' from the appliance 100 as desired and check the level of liquid 120 therein.

Although the cartridge housing 134 of the example cartridge 102' includes a liquid level viewing window 139, in some embodiments, a replaceable cartridge may be provided without such a window 139. In addition, the outer casing 138 may be omitted altogether, such as, for example, as shown in the cartridges 102 of FIG. 1. When provided, the outer casing 138 may have a shape that nests closely with the internal housing body 136. For example, the outer casing 138 and the internal housing body 136 may each have a substantially cylindrical shape concentrically aligned forming a dual layer or dual wall receptacle.

With continued reference to FIG. 5, the internal housing body 136, upper housing cap 137, and outer casing 138 may be fixedly coupled together to define the cartridge housing 134. A cartridge inlet 131 may be provided at a bottom end of the internal housing body 136 to receive a flow of gas (e.g., air) during operation and the cartridge outlet 132 may be provided in the upper housing cap 137 for discharging diffused liquid generated by the cartridge 102' during operation. The cartridge inlet 131 and the cartridge outlet 132 may be aligned along a central axis A defined by the cartridge housing 134. The cartridge housing 134 may be generally rotationally symmetric about the central axis A. For example, as shown in FIG. 5, the cartridge housing 134 may resemble a cylinder or similar receptacle with a mushroom or enlarged top end that is rotationally symmetric about the central axis A. In other instances, the cartridge housing 134 may be asymmetrically shaped and the cartridge inlet 131 and cartridge outlet 132 may not be aligned vertically along a common axis A. Respective caps or plugs 104, 106 may be provided to temporarily close the cartridge inlet 131 and cartridge outlet 132 during storage, transport or the like to prevent fouling or contamination of the cartridge 102' or possible leakage of the liquid 120 contained therein.

Internal components and structures of the cartridge 102' and related functionality will now be described with continued reference to FIG. 5, some of which generally track similar features and functionality disclosed in U.S. Pat. Nos. 9,248,461; 9,162,004; and 10,086,340, which are incorporated by reference in their entireties. According to the illustrated embodiment of the cartridge 102' shown in FIG. 5, the internal components and structures provide, among other things, a flow path through the cartridge 102' from the cartridge inlet 131 to the cartridge outlet 132, as represented by the arrows labeled 130a-130h. When installed in the host diffusion appliance 100, the cartridge inlet 131 is coupled to a source of pressurized gas 121 (e.g., pump 122 of FIG. 4) such that the gas (e.g., air) may be periodically forced through the cartridge 102' as generally represented by the arrows labeled 130a-130h to combine with the liquid 120 and to exit as a gas-liquid mixture comprising particularly small liquid particles carried by the gas, referred to generally herein as a diffused liquid or aerosolized matter. Details of the example pump 122 are not shown or described herein to avoid unnecessarily obscuring descriptions of the embodiments; however, it will be appreciated that the pump 122 may be provided in a wide variety of different form factors.

As shown in FIG. 5, the pressurized gas enters the cartridge 102' through the cartridge inlet 131 at a bottom end of the housing 134 and then flows through a diffusion head 140 provided within the housing 134, which includes a venturi device 142 for drawing the retained liquid 120 into the moving gas stream through an intake conduit 119, after which the gas-liquid mixture moves through a cartridge insert 170 before exiting the cartridge 102' through the cartridge outlet 132. More particularly, the pressurized gas enters the cartridge 102' through the cartridge inlet 131 at a bottom end of the housing 134, as represented by the arrow label 130a, and then flows upwardly through a gas supply conduit 152 defined by a portion of the internal housing body 136, as represented by the arrow labeled 130b. The gas then flows through the venturi device 142 drawing in liquid 120 from a fluid reservoir within the internal housing cavity 135 of the housing 134 via the intake conduit 119 to create a gas-liquid mixture comprising atomized liquid (also referred to herein as diffused liquid or aerosolized matter) that is discharged into an expansion chamber 148 provided by an upper portion 146 of the diffusion head 140, as represented by the arrow labeled 130c. The diffused liquid is then directed toward an impact structure or surface 181 located opposite the venturi device 142 wherein at least some of the diffused liquid impacts and collects on the impact structure or surface 181 and is routed back to any remaining liquid 120 in the fluid reservoir to be reintroduced into the gas stream by the venturi device 142. At least some other of the diffused liquid is redirected to flow down around bulkhead portions 156 of the diffusion head 140 and to pass through passageways 158 in the diffusion head 140 leading to a portion of the internal cavity 135 of the cartridge housing 134 above the fluid level L of liquid 120 in the cartridge 102', as represented by the arrows labeled 130*d* and 130*e*. From there, some of the diffused liquid may collect on the exposed interior surfaces of the housing 134 or other internal structures of the cartridge 102', or otherwise precipitate out of the gas and atomized liquid, and rejoin the liquid 120 in the fluid reservoir to be reintroduced into the gas stream by the venturi device 142. Some other of the diffused liquid may be propelled into the cartridge insert 170 via an inlet 172 thereof, as represented by the arrow labeled 130*f*. From the inlet 172 of the insert 170, the diffused liquid proceeds along a tortuous passage (e.g., a spiral passage) through the cartridge insert 170, as represented by the arrow labeled 130*g*, before passing through an outlet zone of the insert 170 and ultimately the cartridge outlet 132 to be discharged from the cartridge 102', as represented by the arrow labeled 130*h*. In making this convoluted journey from the expansion chamber 148 to the cartridge outlet 132, the liquid particle size distribution of the diffused liquid is refined such that only particularly fine particles are successfully discharged from the cartridge 102' with relatively larger particles collecting on one or more surfaces of the internal structures and components of the cartridge 102', or otherwise precipitating out of the gas, for rejoinder with remaining liquid 120 in the liquid reservoir for reintroduction into the gas stream passing through the venturi device 142.

With continued reference to the example embodiment of the replaceable cartridge shown in FIG. 5, it will be appreciated that the cartridge housing 134 and internal components of the cartridge 102' may define a plurality of distinct chambers downstream of the venturi device 142 through which the diffused liquid sequentially travels before being discharged from the cartridge 102' and ultimately into a surrounding environment. More particularly, the upper portion 146 of the diffusion head 140 and a lower portion of the insert 170 may define a primary expansion chamber 148 immediately above the venturi device 142, a secondary chamber may be provided external of the diffusion head 140 and the insert 170 within the internal cavity 135 of the housing 134 above the fluid level L of the liquid 120 to be diffused, and a tertiary chamber may be provided by the tortuous passage 176 of the insert 170. Passageways or apertures 158 in the upper portion 146 of the diffusion head 140 provide fluid communication between the primary expansion chamber 148 and the secondary chamber. The upper portion 146 of the diffusion head 140 also defines a bulkhead or bulkhead portions 156 that impede the diffused liquid generated by the venturi device 142 from exiting the primary expansion chamber 148 other than through the plurality of passageways or apertures 158. The inlet 172 of the insert 170 provides fluid communication between the secondary chamber and the tertiary chamber (i.e., the tortuous passage 176). Although only one inlet 172 and one tortuous passage 176 is shown providing the sole passage for the diffused liquid to exit the cartridge 102', it is appreciated that a plurality of inlets 172 may be provide to enable diffused liquid to enter one or more tortuous passages leading to the outlet 132 of the cartridge 102. A gasket 174 may also be positioned between an upper end of the insert 170 and the upper housing cap 137 with the gasket 174 forming a cover over the tortuous passage 176.

The distinct chambers described above (i.e., the primary expansion chamber, the secondary chamber and the tertiary chamber) may collectively assist in refining the composition of the diffused liquid to include only the finest liquid particles as the diffused liquid moves sequentially through the chambers during operation. For instance, by the time the gas-liquid mixture exits from cartridge 102', there has been some residence time in each of the distinct chambers to permit undesirably large liquid particles or droplets to precipitate out of or otherwise separate from the mixture and be returned to the liquid reservoir within the internal cavity 135 of the housing 134 for later atomization and dispersion. In this manner, the removable cartridge 102' and components thereof may provide a cartridge solution for a liquid diffusion appliance 100 which has an efficient form factor that is particularly effective at treating spaces with diffused liquid having extremely small liquid particles.

With continued reference to FIG. 5, a liquid retention device 153, such as, for example, an open cell foam plug, may be positioned within the gas supply conduit 152 adjacent the venturi device 142 to retain liquid 120 that may pass downward through the venturi device 142 into the gas supply conduit 152. This may occur during shipping as liquid 120 may move through the intake conduit 119 into the venturi device 142 and unwantedly into the gas supply conduit 152. In addition, it may occur when stopping the flow of air through the cartridge 102' which may result in some of the liquid expelled into the expansion chamber 148 settling back down into and passing through the venturi device 142. The liquid retention device 153 may collect liquid 120 that unwantedly passes into the gas supply conduit 152 and retain the liquid 120 therein until the cartridge 102' is used again, at which time the air flowing through the cartridge 102' may clear the liquid 120 from the liquid retention device 153.

With continued reference to FIG. 5, the replaceable cartridge 102' may further comprise an integrated circuit 180 coupled to the cartridge housing 134, the integrated circuit including memory to store cartridge data associated with the replaceable cartridge 102. The cartridge data may include, for example, a type of liquid 120 stored in the cartridge 102', an amount of liquid 120 stored in the cartridge, a cartridge identifier from which to authenticate the cartridge 102', and/or other data. The amount of liquid 120 may be measured directly, indirectly or otherwise estimated by usage history data or other techniques. For example, duration and intensity history data associated with the operation of the host appliance 100 and a particular cartridge 102' may be logged and used to estimate the amount of liquid 120 remaining in the cartridge 102'.

As shown in FIG. 5, the integrated circuit 180 may be embedded in or otherwise coupled to a cartridge printed circuit board (PCB) 182. The cartridge PCB 182 may be coupled to the cartridge housing 134, such as, for example, by adhesive or other joining techniques or devices. According to the example embodiment of the cartridge 102' shown in FIG. 5, the cartridge PCB 182 is located at a bottom end of the cartridge housing 134 and has an annular shape that nests with the bottom end of the cartridge housing 134. The cartridge PCB 182 further comprises an electrical interface 184 in electrical communication with the integrated circuit 180 to enable retrieval of the cartridge data by an external system contacting the electrical interface 184.

Further details of the air scenting appliance 100 and components thereof will now be described with reference to FIGS. 1 through 4. As previously described, the air scenting appliance 100 includes a replaceable cartridge 102 containing liquid 120 to be aerosolized and discharged through a cartridge outlet 132, a pump 122 operatively coupled to the replaceable cartridge 102 to supply air to the replaceable cartridge 102 to generate the aerosolized compound from the liquid 120, a control system 128 operatively coupled to the pump 122 for controlling the pump 122 to supply the air to the replaceable cartridge 102 to generate the aerosolized compound and discharge the aerosolized compound from the cartridge outlet 132, and an appliance housing 101 that accommodates the replaceable cartridge 102, the pump 122 and the control system 128 therewithin. A foam enclosure 123 or other sound deadening or muffling device may also be provided to surround the pump 122 and suppress or reduce noise generated by the pump 122 during operation.

With reference to FIGS. 1 through 4, the air scenting appliance 100 may have a generally or overall cylindrical shape having a vertical central longitudinal axis. The air scenting appliance 100 may be designed, configured, sized, and shaped for operation within a motor vehicle, and to fit in particular within a cup holder within the motor vehicle. The air scenting appliance 100 may include a form factor that is adaptable and/or adjustable to cup holders of different sizes.

For example, the air scenting appliance 100 may include a sleeve 202 that extends around and surrounds a bottom portion of the air scenting appliance 100. In particular, the sleeve 202 may have an inner surface configured to lie flush against an outer surface of a housing 101 of the air scenting appliance 100 and an outer surface configured to engage with a surface of a cup holder 110 within a motor vehicle. For example, the sleeve 202 may have an overall annular or hollow cylindrical shape and may include a plurality of compressible or elastically deformable features such as protrusions or ridges 204 that protrude radially outward from the cylindrical shape of the sleeve 202 and that extend longitudinally along a height of the sleeve 202. The ridges 204 may be configured to engage with the surface of the cup holder 110 to snugly mount the air scenting appliance 100 within the cup holder 110, and may compress or deform to different degrees to adapt to slight variations in size of conventional cup holders 110. In some embodiments, the sleeve 202 may include one, two, three, four, five, six, eight, ten, or more of the ridges 204, and the ridges 204 may be equally spaced apart from one another around the circumference of the sleeve 202. In some embodiments, the air scenting appliance 100 may be provided with a plurality of different sleeves 202, each of the sleeves 202 having a different size (e.g., a different overall diameter or protrusions of different radial depths). In such embodiments, a user of the air scenting device 100 can select one of the plurality of sleeves 202 based on its fit within a particular cup holder 110 of his or her vehicle or vehicles.

With continued reference to FIGS. 1 through 4, the air scenting appliance 100 may include an electrical port 206, which may be a USB port, such as a USB Type-C port, through which the air scenting appliance 100 may be communicatively coupled to other electronic devices, such as a built-in electronic component of the automobile, and through which the air scenting appliance 100 may receive sufficient electrical power to drive its operation from other electronic devices, such as the built-in electronic component of the automobile. As illustrated in the figures, the port 206 may be located in a bottom portion of the air scenting appliance 100 and may be accessible from underneath the air-treatment appliance 100, such that when the air scenting appliance 100 is resting on a flat surface, the port 206 is hidden and not visible. As further illustrated in the figures, the air scenting appliance 100 may include a groove 208 that extends from the port 206, horizontally along a bottom end of the air scenting appliance 100, and vertically along an outer side surface of the air scenting appliance 100, such as along more than half the height of the air scenting appliance 100. In some embodiments, the sleeve 202 can extend over and around the groove 208 when the sleeve 202 is positioned on the air scenting appliance 100, and the groove 208 can extend to a location above a top end of the sleeve 202. When the air scenting appliance 100 is in use, a power and/or communications cable 112 (FIG. 1) can be plugged into the port 206 and extend from the port 206 through the groove 208, between an outer surface of the housing 101 of the air scenting appliance 100 and an inner surface of the sleeve 202, outward from the groove 208 at a location above the top end of the sleeve 202, and to another electronic device such as an electronic system and/or power supply system of a host vehicle.

As also illustrated in FIGS. 1 through 4, the air scenting appliance 100 may include a ring-shaped or annular dial 107 that extends around an outer periphery of a top end portion of the air scenting appliance 100. The dial 107 may be configured to be rotated with respect to the rest of the air scenting appliance 100 by a user of the air scenting appliance 100 to adjust a flow rate of air through the air scenting appliance 100 and thereby adjust an intensity of scents produced by the air scenting appliance 100. For example, the dial 107 may have a protrusion 108 that allows a user to more securely hold and more easily rotate the dial 107 and/or that provides a physical indication of the location of the dial 107 within its range of motion. Thus, if a person wants to adjust operation of the air scenting appliance 100 while driving a motor vehicle, the person can easily do so. Thus, it can be said that the dial 107 allows "blind" operation of the air scenting device 100. In some implementations, the dial 107 may provide haptic feedback and/or audible feedback to the user as it is rotated. For example, the dial 107 may be coupled to the rest of the air scenting appliance 100 by a plurality of detents or other mechanical features that provide haptic and/or audible feedback (e.g., clicks) as the dial 107 is turned. The appliance 100 may further include a vibration device to provide a vibration or vibrations indicative of changes in intensity settings. A speaker may be provided in some embodiments to provide audible feedback. The feedback may change in duration, intensity or other characteristics with increases in the intensity level, such as from level 0 (no output) to level 10 (maximum output). The changes in intensity level may be stepwise or continuous. Likewise, characteristics of the audible and/or haptic feedback may correspondingly change in a stepwise or continuous manner.

As illustrated in FIG. 4, an inner surface of the dial 107 may include a plurality of teeth 214 and the air scenting appliance 100 may include a gear 216 or other rotary member having teeth complementary to the teeth 214 of the dial 107. The gear 216 may be coupled to a printed circuit board 218 or otherwise in communication with the printed circuit board 218 of the control system 128 such that rotation of the gear 216 provides a signal to components coupled to or integrated within the printed circuit board 218, which can be used to control operation of other components of the air scenting appliance 100, such as of the pump 122. The dial 107 may also include rotational stops 215 to define and limit the range of motion of the dial 107 relative to the housing 101.

In some embodiments, the air scenting appliance 100 may include one or more accelerometers, such as a three-axis accelerometer, or other sensor which may be coupled to or integrated within the printed circuit board 218. Thus, when the air scenting appliance 100 is located within a motor vehicle, the accelerometer(s) or other sensor may provide signals indicating that the motor vehicle is operating and in motion. In such embodiments, these signals may be used to turn the air scenting appliance 100 on and off, and/or from a sleep mode to an active mode. For example, the air scenting appliance 100 may be operated in an "automatic" mode, in which the air scenting appliance 100 is modified to an active mode when the signal(s) provided by the accelerometer(s) indicate that the vehicle is in motion, and the air scenting appliance 100 is turned off automatically or modified to a sleep mode when the signal(s) provided by the accelerometer(s) indicate that the vehicle is not in motion. In some embodiments, the air scenting appliance 100 is turned on or modified to an active mode when the signal(s) provided by the accelerometer(s) indicate that the vehicle has been in motion for a threshold period of time, such as 15 seconds, 30 seconds, 1 minute, or 2 minutes, and the air scenting appliance 100 is turned off automatically or modified to a sleep mode when the signal(s) provided by the accelerometer(s) indicate that the vehicle has not been in motion for a threshold period of time, such as 1 minute, 2 minutes, or 5 minutes.

In addition, the air scenting appliance 100 may include one or more accelerometers, such as a three-axis accelerometer, or other sensor, such as a level sensor, which may be coupled to or integrated within the printed circuit board 218 to sense or determine the orientation of the appliance 100. For example, the one or more accelerometers or level sensor may be used to determine whether the appliance 100 is an upright position or generally upright position (e.g., within 5°, 10°, 15° or 20° from vertical) that is suitable for dispensing scent, or not in an upright position or generally upright position. The air scenting appliance 100 may be modified to or maintained in an active mode when the signal(s) provided by the accelerometer(s) or level sensor indicate that the appliance 100 is in the upright or generally upright position, and the appliance 100 may be turned off automatically or modified to a sleep mode or otherwise deactivated when the signal(s) provided by the accelerometer(s) or level sensor indicate that the appliance 100 is not in the upright or generally upright position. In this manner, the appliance 100 may be turned off, disabled or otherwise prevented from discharging scent when upended or positioned on its side, for example.

In some embodiments, the air scenting appliance 100 may also be operated in a "manual" mode, in which the air scenting appliance 100 is turned on and off by an operator interacting with a switch, button, or other physical interface device of the air scenting appliance 100, such as the dial 107. In some embodiments, the air scenting appliance 100 may include a switch, button, or other physical interface device that allows the operator to switch between the "automatic" and "manual" modes of operation, or simply to enable or disable the "automatic" mode of operation. In the "manual" made of operation, the appliance 100 may, in some embodiments, still be transitioned to an off or sleep state or otherwise deactivated if the appliance 100 is not detected to be in an upright or generally upright position. In such instances, the appliance 100 may be reactivated by positioning the appliance 100 in an upright or generally upright position.

Figure 6:
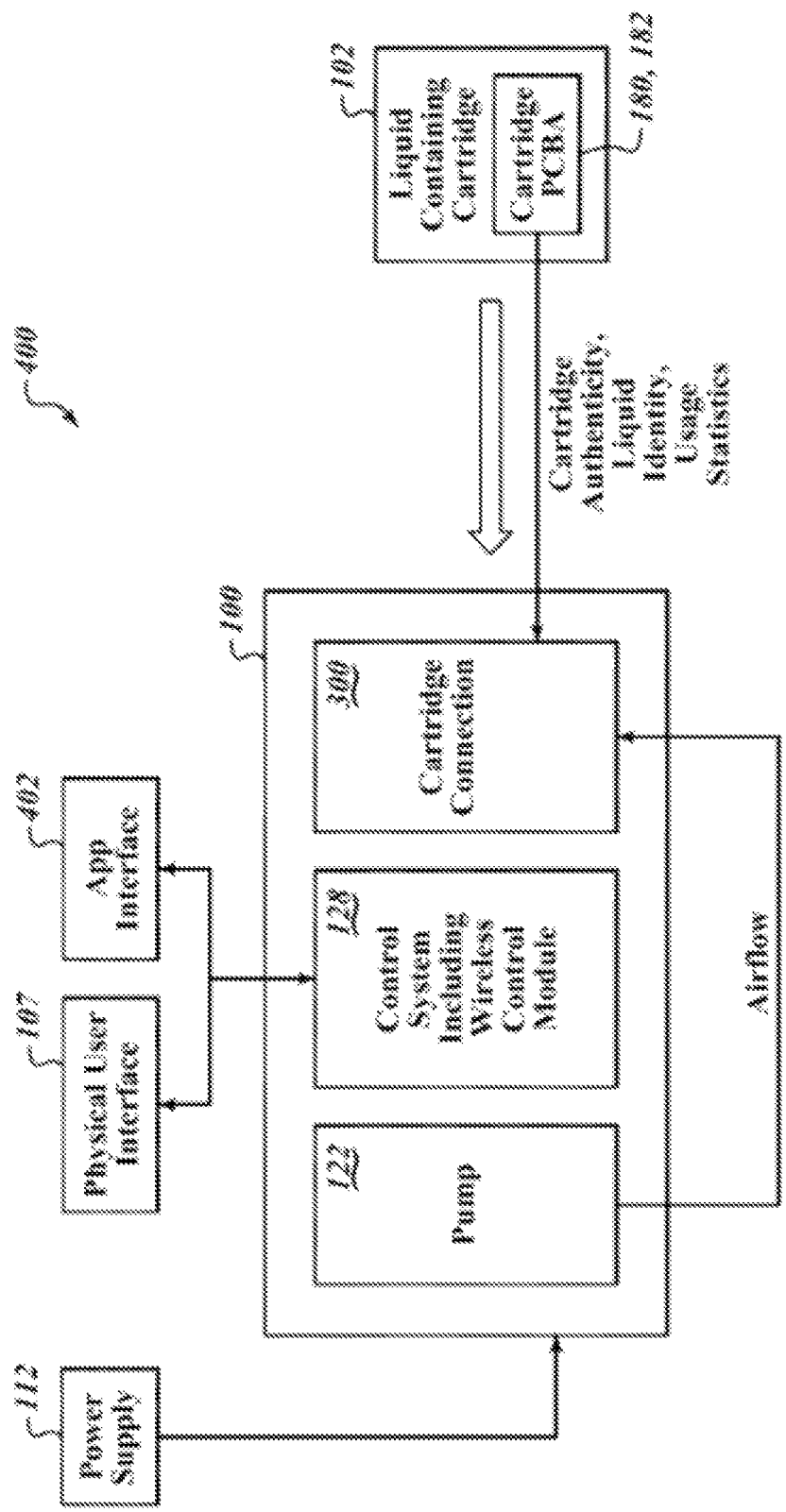
FIG. 6 is a system diagram, according to an example embodiment, of an air treatment system that includes an air treatment appliance and a replaceable cartridge therefor.

FIG. 6 provides a system diagram, according to one example embodiment, of an air scenting system 400 comprising an air scenting appliance, such as, for example, the example embodiment of the air scenting appliance 100 described above with reference to FIGS. 1 through 4, and a replaceable cartridge installable in the appliance 100 and containing a liquid to be discharged as aerosolized matter, such as the replaceable cartridge 102, 102' shown in FIGS. 1 and 5. As can be appreciated from a review of FIG. 6, the appliance 100 may include a control system 128 that is configured to receive one or more control inputs from a physical user interface (e.g., dial 107) of the appliance 100 and/or an application interface 402, which may be provided via a smartphone or other computing device to control the appliance 100 remotely. The control system 128 is operatively coupled to an air source (e.g., pump 122) for supplying air flow through the cartridge 102 for generating the aerosolized matter from the liquid contained in the cartridge 102 for discharge into the surrounding environment within a vehicle. In some instances, the cartridge 102 may include a cartridge PCB 182 and an associated integrated circuit 180 for storing cartridge information and enabling the transfer of information between the cartridge 102 and the control system 128 to provide enhanced functionality. In some particularly advantageous embodiments, cartridge information may be obtained by the control system 128 and transmitted to a remote device or devices, such as a smartphone, for displaying various indications, alerts or other information to a user of the appliance 100 based at least in part on the information stored by the cartridge 102 and/or control system 128 of the appliance 100.

It may be noted that the air scenting appliances 100, replaceable cartridges 102, and components thereof disclosed herein may include operational control via control system 128 for varying the pressure, flow velocity and/or timing of operation of the onboard air source (e.g., pump 122) to provide air flow through the cartridge 102. In addition to using the control system 128 to alter the amount of liquid diffused or aerosolized by the appliance 100 and the corresponding degree of treatment of a space, the control system 128 may be used to provide other functionality.

As previously described, the control system 128 may also be in communication with one or more accelerometers or other sensors for detecting motion of a host vehicle and providing enhanced functionality in view of the same. The control system 128 may also be in communication with one or more accelerometers or other sensors, such as a level sensor, for detecting the orientation of the appliance and providing enhanced functionality in view of the same.

In addition, in some instances, the appliance 100 may be communicatively coupled (directly or wirelessly) to an onboard computing and/or control system of the vehicle. In this manner, the appliance 100 may be configured to receive signals from the vehicle indicative of airflow or other conditions within the interior of the vehicle (such as air handler fan speed) and may be configured to adjust operational parameters of the appliance (e.g., intensity level) in accordance with such signals from the vehicle. For example, in an embodiment of such a connected appliance, the appliance may receive an indication of vehicle motion from the onboard computing and/or control system of the vehicle and transition between an active mode and sleep mode based on the same, and/or may vary an operational characteristic of the appliance, such as scent intensity, based at least in part on the same.

In connection with the embodiments described herein, it will be also appreciated that various related methods may be provided. For example, one example method implemented by a processor-based electronic liquid diffusion device, such as, for example, the appliance 100 of FIG. 1, may be summarized as including: detecting motion or the absence of motion of a host vehicle; and modifying an operational state of the electronic liquid diffusion device based at least in part on the detected motion or the absence of motion. Modifying the operational state of the electronic liquid diffusion device may include transitioning the operational state from an "active mode" in which aerosolized matter may be discharged from the device to a "sleep mode" in which aerosolized matter is unable to be discharged from the device, or vice versa. The transitioning of the operational state may occur after a threshold period of time in which the motion or absence of motion is detected.

Another example method implemented by a processor-based electronic liquid diffusion device, such as, for example, the appliance 100 of FIG. 1, may be summarized as including: detecting an orientation of the electronic liquid diffusion device; and modifying an operational state of the electronic liquid diffusion device based at least in part on the detected orientation of the appliance. Modifying the operational state of the electronic liquid diffusion device may include transitioning the operational state from an "active mode" in which aerosolized matter may be discharged from the device to a "sleep mode" in which aerosolized matter is unable to be discharged from the device, or vice versa. The operational state of the electronic liquid diffusion device may be transitioned to a "sleep mode" or otherwise disabled, for example, when the orientation of the appliance is detected not in an upright or generally upright position.

Yet another example method implemented by a processor-based electronic liquid diffusion device, such as, for example, the appliance 100 of FIG. 1, may be summarized as including: receiving a signal from an onboard computing and/or control system of a vehicle related to a characteristic or operational parameter of the vehicle, a vehicle component or an environment of the vehicle; and modifying the operational state of the electronic liquid diffusion device based at least in part on the received signal. Modifying the operational state of the electronic liquid diffusion device may include transitioning the operational state from an "active mode" in which aerosolized matter may be discharged from the device to a "sleep mode" in which aerosolized matter is unable to be discharged from the device, or vice versa. The operational state of the electronic liquid diffusion device may be transitioned to a "sleep mode" or otherwise disabled, for example, when the appliance receives a signal from the vehicle indicative of the vehicle being parked or turned off. Modifying the operational state of the electronic liquid diffusion device may include, for example, adjusting an intensity level of the appliance based at least in part in changes in air handler fan speed.

Again, although certain specific details are set forth in order to provide a thorough understanding of various disclosed embodiments, one skilled in the relevant art will recognize that embodiments may be practiced without one or more of these specific details. Moreover, aspects and features of the various embodiments described above can be combined to provide further embodiments. All of the U.S. patents referred to in this specification and listed in the Application Data Sheet, including but not limited to U.S. provisional patent application No. 63/173,475, filed Apr. 11, 2021, are incorporated herein by reference, in their entirety. Aspects of the embodiments can be modified, if necessary to employ features, structures, functionality or concepts of the various patents to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled.

The invention claimed is:

1. An air scenting appliance, comprising:
a form factor configured to be insertably received in a cup holder of a vehicle, and including:
 a housing comprising a rigid material and containing one or more functional components of the air scenting appliance; and
 a sleeve comprising a compressible and/or an elastically deformable material, the sleeve being separate and distinct from the housing and surrounding at least a lower portion of the housing to assist in fitting the air scenting appliance within the cup holder.

2. An air scenting appliance, comprising:
a form factor configured to be insertably received in a cup holder of a vehicle, and including:
 a housing containing one or more functional components of the air scenting appliance; and
 a sleeve separate and distinct from the housing and surrounding at least a lower portion of the housing to assist in fitting the air scenting appliance within the cup holder,
 wherein the sleeve includes at least one elastically deformable feature to provide a variable effective outer diameter as the elastically deformable feature is deformed between the cup holder and the housing when the air scenting appliance is positioned in the cup holder for use.

3. The air scenting appliance of claim 2, wherein the elastically deformable feature includes a longitudinal channel extending along at least a majority of a height of the sleeve.

4. The air scenting appliance of claim 3, wherein an elongate void is formed between the elastically deformable feature of the sleeve and the housing of the appliance, the elongate void varying in volume as the elastically deformable feature is deformed.

5. The air scenting appliance of claim 2, wherein the sleeve includes a plurality elastically deformable features spaced circumferentially about the sleeve.

6. An air scenting appliance, comprising:
a form factor configured to be insertably received in a cup holder of a vehicle, and including:
 a housing containing one or more functional components of the air scenting appliance; and
 a sleeve separate and distinct from the housing and surrounding at least a lower portion of the housing to assist in fitting the air scenting appliance within the cup holder,
 wherein the housing comprises a longitudinally extending sidewall and a power supply cable groove formed in an outer surface of the longitudinally extending sidewall for routing a power supply cable from a lower end of the appliance toward an upper end of the appliance along the longitudinally extending sidewall.

7. The air scenting appliance of claim 6, wherein the power supply cable groove extends along the longitudinally extending sidewall for at least a majority of a height of the housing.

8. The air scenting appliance of claim 6, wherein at least a majority of the power supply cable groove is concealed by the sleeve.

9. The air scenting appliance of claim 6, wherein the sleeve includes at least one elastically deformable feature to provide a variable effective outer diameter as the elastically deformable feature is deformed between the cup holder and the housing when the air scenting appliance is positioned in the cup holder for use, and wherein the elastically deformable feature is aligned with and runs parallel to the power supply cable groove.

10. An air scenting appliance, comprising:
a form factor configured to be insertably received in a cup holder of a vehicle, and including:
   a housing containing one or more functional components of the air scenting appliance; and
   a dial rotatably coupled to the housing to adjust an intensity level of the scented matter discharged from the appliance during use,
   wherein the appliance is configured to provide a haptic feedback and/or an audible feedback to a user of the appliance as the dial is rotated to adjust the intensity level of the scented matter discharged from the appliance during use.

11. An air scenting appliance, comprising:
a form factor configured to be insertably received in a cup holder of a vehicle, and including:
   a housing containing one or more functional components of the air scenting appliance; and
   a dial rotatably coupled to the housing to adjust an intensity level of the scented matter discharged from the appliance during use,
   wherein the dial includes an exterior longitudinal surface that transitions smoothly to an exterior longitudinal surface of the housing to provide a collective surface that is interrupted only by a seam between the dial and the housing.

12. An air scenting appliance, comprising:
a form factor configured to be insertably received in a cup holder of a vehicle, and including:
   a housing containing one or more functional components of the air scenting appliance; and
   a dial rotatably coupled to the housing to adjust an intensity level of the scented matter discharged from the appliance during use,
   wherein the exterior longitudinal surface of the dial and the exterior longitudinal surface of the housing collectively form a flared cylinder surface with a variable draft angle.

13. An air scenting appliance, comprising:
a form factor configured to be insertably received in a cup holder of a vehicle, and including:
   a housing containing one or more functional components of the air scenting appliance; and
   a dial rotatably coupled to the housing to adjust an intensity level of the scented matter discharged from the appliance during use,
   wherein the dial includes a set of teeth on an inner circumferential side thereof which engage a rotational gear provided in the housing to generate an intensity control signal as the rotational gear rotates in response to a position of the dial.

14. An air scenting appliance, comprising:
a form factor configured to be insertably received in a cup holder of a vehicle, and including:
   a housing containing one or more functional components of the An air scenting appliance; and
   a dial rotatably coupled to the housing to adjust an intensity level of the scented matter discharged from the appliance during use,
   wherein the dial is configured to rotate around a replaceable scent cartridge receivable in the air scenting appliance while the replaceable scent cartridge is held static within the housing to adjust the intensity level of the scented matter discharged from the appliance during use.

15. An air scenting appliance, comprising:
a form factor configured to be insertably received in a cup holder of a vehicle; and
a control system operable to discharge scented matter from the appliance in a controlled manner, the control system including at least one accelerometer or other sensor that is configured to sense motion of the vehicle,
wherein the control system is configured to modify an operational mode of the appliance based at least in part on a signal derived from the at least one accelerometer or other sensor.

16. The air scenting appliance of claim 15 wherein the operational mode of the appliance is automatically transitioned to a sleep mode when the at least one accelerometer or other sensor fails to detect any motion of the vehicle during a threshold duration.

17. The air scenting appliance of claim 15 wherein the operational mode of the appliance is automatically transitioned from a sleep mode to an active mode when the at least one accelerometer or other motion sensing device detects motion of the vehicle.

18. An air scenting appliance configured, comprising:
a form factor configured to be insertably received in a cup holder of a vehicle; and
a control system operable to discharge scented matter from the appliance in a controlled manner, the control system including at least one accelerometer or level sensor that is configured to sense orientation of the appliance,
wherein the control system is configured to modify an operational mode of the appliance based at least in part on a signal derived from the at least one accelerometer or level sensor indicative of an orientation of the appliance.

19. The air scenting appliance of claim 18 wherein the operational mode of the appliance is automatically transitioned to a sleep mode or powered off when the at least one accelerometer or level sensor detects that the appliance is not positioned in an upright orientation or generally upright orientation.

* * * * *

UNITED STATES PATENT AND TRADEMARK OFFICE
CERTIFICATE OF CORRECTION

PATENT NO. : 12,011,519 B2  
APPLICATION NO. : 18/128091  
DATED : June 18, 2024  
INVENTOR(S) : Nathan Sward et al.

Page 1 of 1

It is certified that error appears in the above-identified patent and that said Letters Patent is hereby corrected as shown below:

In the Claims

<u>Column 18, Claim 14, Line 8:</u>  
"of the An air scenting"  
Should read:  
--of the air scenting--.

Signed and Sealed this  
Twenty-fourth Day of September, 2024

Katherine Kelly Vidal  
*Director of the United States Patent and Trademark Office*